United States Patent
Wechter et al.

(12)

(10) Patent No.: US 9,649,489 B2
(45) Date of Patent: May 16, 2017

(54) ELECTRICAL STIMULATION LEADS AND SYSTEMS WITH ANCHORING UNITS HAVING STRUTS AND METHODS OF MAKING AND USING

(71) Applicant: Boston Scientific Neuromodulation Corporation, Valencia, CA (US)

(72) Inventors: David Ernest Wechter, Santa Clarita, CA (US); John M. Barker, Ventura, CA (US); Jacob B. Leven, Huntington Beach, CA (US); Ryan Michael Baca, Arleta, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/726,233

(22) Filed: May 29, 2015

(65) Prior Publication Data
US 2015/0343199 A1    Dec. 3, 2015

Related U.S. Application Data

(60) Provisional application No. 62/006,824, filed on Jun. 2, 2014, provisional application No. 62/111,596, filed on Feb. 3, 2015.

(51) Int. Cl.
*A61N 1/00* (2006.01)
*A61N 1/05* (2006.01)

(52) U.S. Cl.
CPC .................. *A61N 1/0558* (2013.01)

(58) Field of Classification Search
CPC ................ A61N 1/05; A61N 1/0558

USPC .................................... 607/116, 128
See application file for complete search history.

(56) References Cited

U.S. PATENT DOCUMENTS

| | | | |
|---|---|---|---|
| 3,754,555 | A | 8/1973 | Schmitt |
| 3,814,104 | A | 6/1974 | Irnich |
| 4,112,952 | A | 9/1978 | Thomas et al. |
| 4,280,512 | A | 7/1981 | Karr et al. |

(Continued)

FOREIGN PATENT DOCUMENTS

| | | |
|---|---|---|
| WO | 2004028618 | 4/2004 |
| WO | 2005028023 | 3/2005 |

(Continued)

OTHER PUBLICATIONS

U.S. Appl. No. 62/006,824, filed Jun. 2, 2014.
(Continued)

*Primary Examiner* — Nadia A Mahmood
(74) *Attorney, Agent, or Firm* — Lowe Graham Jones PLLC; Bruce E. Black

(57) ABSTRACT

An anchoring unit is disposed on a lead body of an electrical stimulation lead. The anchoring unit has a first end and a second end and includes a first attachment ring disposed at the first end, a second attachment ring disposed at the second end, and longitudinal struts extending linearly between, and coupled to, the first and second attachment rings. At least a portion of each longitudinal strut rests against the lead body in a retracted position, and each anchoring unit has a deployed position in which the first and second attachment rings are positioned closer together with the longitudinal struts extending away from the lead body to contact patient tissue and anchor the lead within the patient tissue.

19 Claims, 12 Drawing Sheets

(56) References Cited

U.S. PATENT DOCUMENTS

| | | |
|---|---|---|
| 4,378,023 A | 3/1983 | Trabucco |
| 4,407,303 A | 10/1983 | Akerstrom |
| 4,519,404 A | 5/1985 | Fleischhacker |
| 4,706,682 A | 11/1987 | Stypulkowski et al. |
| 4,721,118 A | 1/1988 | Harris |
| 4,913,147 A | 4/1990 | Fahlstrom et al. |
| 5,052,407 A | 10/1991 | Hauser et al. |
| 5,314,462 A | 5/1994 | Heil, Jr. et al. |
| 5,325,870 A | 7/1994 | Kroll et al. |
| 5,374,279 A | 12/1994 | Duffin, Jr. et al. |
| 5,466,255 A | 11/1995 | Franchi |
| 5,492,119 A | 2/1996 | Abrams |
| 5,507,802 A | 4/1996 | Imran |
| 5,571,162 A | 11/1996 | Lin |
| 5,609,623 A | 3/1997 | Lindegren |
| 5,674,273 A | 10/1997 | Helland |
| 5,824,030 A | 10/1998 | Yang et al. |
| 5,868,741 A | 2/1999 | Chia et al. |
| 5,871,532 A | 2/1999 | Schroeppel |
| 5,922,014 A | 7/1999 | Warman et al. |
| 5,948,014 A | 9/1999 | Valikai |
| 5,957,966 A | 9/1999 | Schroeppel et al. |
| 6,093,185 A | 7/2000 | Ellis et al. |
| 6,181,969 B1 | 1/2001 | Gord |
| 6,181,973 B1 | 1/2001 | Ceron et al. |
| 6,249,708 B1 | 6/2001 | Nelson et al. |
| 6,345,198 B1 | 2/2002 | Mouchawar et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,671,544 B2 | 12/2003 | Baudino |
| 6,741,892 B1 | 5/2004 | Meadows et al. |
| 6,999,819 B2 | 2/2006 | Swoyer et al. |
| 7,130,700 B2 | 10/2006 | Gardeski et al. |
| 7,187,983 B2 | 3/2007 | Dahlberg et al. |
| 7,244,150 B1 | 7/2007 | Brase et al. |
| 7,328,068 B2 | 2/2008 | Spinelli et al. |
| 7,343,202 B2 | 3/2008 | Mrva et al. |
| 7,369,894 B2 | 5/2008 | Gerber |
| 7,437,193 B2 | 10/2008 | Parramon et al. |
| 7,565,198 B2 | 7/2009 | Bennett et al. |
| 7,672,734 B2 | 3/2010 | Anderson et al. |
| 7,761,165 B1 | 7/2010 | He et al. |
| 7,835,801 B1 | 11/2010 | Sundararajan et al. |
| 7,881,783 B2 | 2/2011 | Bonde et al. |
| 7,899,550 B1 | 3/2011 | Doan et al. |
| 7,927,282 B2 | 4/2011 | Hettrick et al. |
| 7,949,395 B2 | 5/2011 | Kuzma |
| 7,974,706 B2 | 7/2011 | Moffitt et al. |
| 8,096,959 B2 | 1/2012 | Stewart et al. |
| 8,175,710 B2 | 5/2012 | He |
| 8,224,450 B2 | 7/2012 | Brase |
| 8,364,278 B2 | 1/2013 | Pianca et al. |
| 8,452,420 B2 | 5/2013 | Flach et al. |
| 8,469,954 B2 | 6/2013 | Young et al. |
| 8,532,789 B2 | 9/2013 | Smits |
| 2002/0151867 A1 | 10/2002 | McGuckin, Jr. et al. |
| 2002/0156058 A1 | 10/2002 | Borkan |
| 2003/0195600 A1 | 10/2003 | Tronnes et al. |
| 2004/0116992 A1 | 6/2004 | Wardle et al. |
| 2004/0230279 A1 | 11/2004 | Cates et al. |
| 2005/0288722 A1 | 12/2005 | Eigler et al. |
| 2007/0043414 A1 | 2/2007 | Fifer et al. |
| 2007/0049980 A1 | 3/2007 | Zielinski et al. |
| 2007/0150036 A1 | 6/2007 | Anderson |
| 2007/0179583 A1 | 8/2007 | Goetzinger et al. |
| 2007/0293923 A1 | 12/2007 | Soltis et al. |
| 2008/0103569 A1 | 5/2008 | Gerber |
| 2008/0103572 A1 | 5/2008 | Gerber |
| 2008/0167701 A1 | 7/2008 | John et al. |
| 2008/0183253 A1* | 7/2008 | Bly ............... A61N 1/0558 607/116 |
| 2008/0183266 A1 | 7/2008 | D'Aquanni et al. |
| 2009/0012592 A1 | 1/2009 | Buysman et al. |
| 2009/0023975 A1* | 1/2009 | Marseille .......... A61B 17/3421 600/16 |
| 2009/0054949 A1 | 2/2009 | Alexander et al. |
| 2009/0248095 A1 | 10/2009 | Schleicher et al. |
| 2009/0254151 A1 | 10/2009 | Anderson et al. |
| 2009/0276023 A1* | 11/2009 | Morris ............... A61N 1/0558 607/116 |
| 2010/0131036 A1 | 5/2010 | Geistert et al. |
| 2010/0168806 A1 | 7/2010 | Norlin-Weissenrieder et al. |
| 2010/0256696 A1 | 10/2010 | Schleicher et al. |
| 2011/0251662 A1 | 10/2011 | Griswold et al. |
| 2011/0313427 A1 | 12/2011 | Gindele et al. |
| 2012/0053665 A1 | 3/2012 | Stolz et al. |
| 2012/0323253 A1 | 12/2012 | Garai et al. |
| 2013/0066411 A1 | 3/2013 | Thacker et al. |
| 2013/0218127 A1 | 8/2013 | Rosenberg et al. |
| 2014/0330287 A1 | 11/2014 | Thompson-Nauman et al. |
| 2014/0343645 A1 | 11/2014 | Wechter |
| 2014/0343656 A1 | 11/2014 | Wechter |
| 2015/0039069 A1 | 2/2015 | Rys et al. |
| 2015/0051616 A1 | 2/2015 | Haasl et al. |

FOREIGN PATENT DOCUMENTS

| | | |
|---|---|---|
| WO | 2013082283 | 6/2013 |
| WO | 2015167800 | 11/2015 |

OTHER PUBLICATIONS

U.S. Appl. No. 14/634,253, filed Feb. 27, 2015.
U.S. Appl. No. 62/111,596, filed Feb. 3, 2015.
U.S. Appl. No. 14/690,071, filed Apr. 17, 2015.
U.S. Appl. No. 14/726,233, filed May 29, 2015.

* cited by examiner

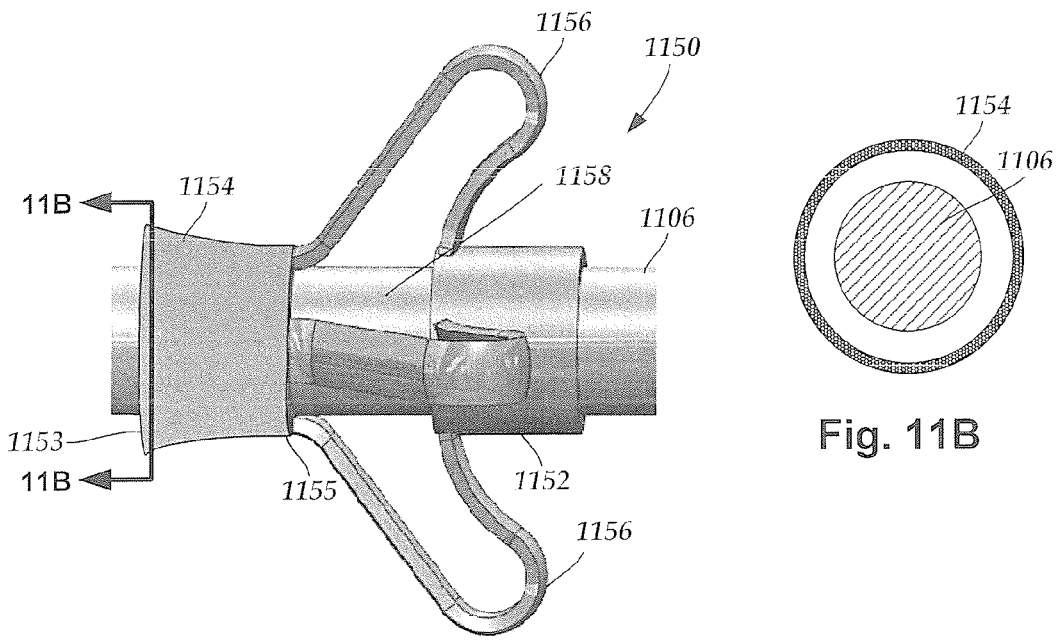
Fig. 11A
Fig. 11B
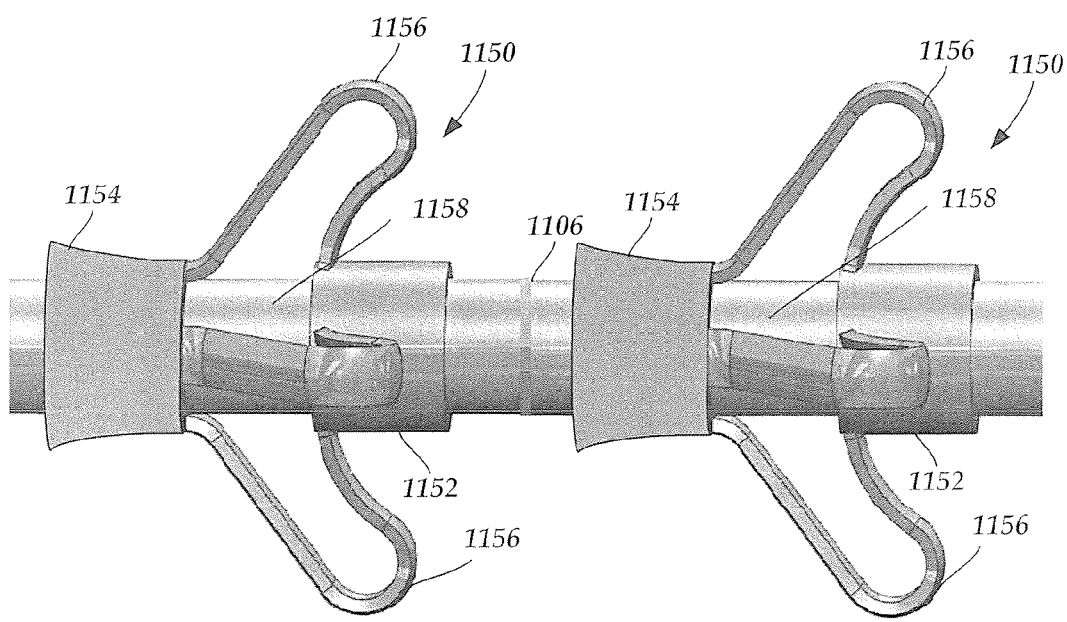
Fig. 11C

ELECTRICAL STIMULATION LEADS AND SYSTEMS WITH ANCHORING UNITS HAVING STRUTS AND METHODS OF MAKING AND USING

CROSS-REFERENCE TO RELATED APPLICATIONS

This application claims the benefit under 35 U.S.C. §119 (e) of U.S. Provisional Patent Application Ser. No. 62/006,824 filed Jun. 2, 2014, and U.S. Provisional Patent Application Ser. No. 62/111,596, filed Feb. 3, 2015, both of which are incorporated herein by reference.

FIELD

The present invention is directed to the area of implantable electrical stimulation systems and methods of making and using the systems, and in particular implantable electrical stimulation leads having anchoring units with longitudinal struts and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

One concern regarding implanted leads is lead migration. This may occur over time and result in movement of the lead away from the desired tissue for stimulation so as to reduce the effectiveness of therapeutic treatment.

BRIEF SUMMARY

One embodiment is an anchoring unit having a first end and a second end. The anchoring unit includes a first attachment ring disposed at the first end to receive a first portion of a lead within the first attachment ring; a second attachment ring disposed at the second end to receive a second portion of the lead within the second attachment ring; and longitudinal struts extending linearly between, and coupled to, the first and second attachment rings.

Another embodiment is an electrical stimulation lead including a lead body having a distal end portion and a proximal end portion; electrodes disposed along the distal end portion of the lead body; terminals disposed along the proximal end portion of the lead body; conductors disposed within the lead body and coupling the terminals to the electrodes; and an anchoring unit disposed along the distal end portion of the lead body. The anchoring unit has a first end and a second end and includes a first attachment ring disposed at the first end, a second attachment ring disposed at the second end, and longitudinal struts extending linearly between, and coupled to, the first and second attachment rings. At least a portion of each longitudinal strut rests against the lead body in a retracted position, and each anchoring unit is configured and arranged to have a deployed position in which the first and second attachment rings are positioned closer together with the longitudinal struts extending away from the lead body to contact patient tissue and anchor the lead within the patient tissue.

In at least some embodiments, the anchoring unit is disposed proximal to all of the electrodes. In at least some embodiments, the anchoring unit is configured and arranged such that, in the deployed position, the longitudinal struts extend perpendicularly away from the lead body. In at least some embodiments, the anchoring unit further includes an extension portion extending from the first attachment ring to the proximal end portion of the lead and configured and arranged for manual operation by a user when the distal end portion of the lead is implanted. In at least some embodiments, the extension portion is formed as a single piece with the first attachment ring.

In at least some embodiments, the anchoring unit is configured and arranged to preferentially adopt the deployed position unless constrained to adopt the retracted position. In at least some embodiments, one of the first attachment ring or second attachment ring is fixed to the lead body and another one of the first attachment ring and the second attachment ring is slidably engaged around the lead body. In at least some embodiments, the longitudinal struts are configured and arranged to angle toward the proximal end portion of the lead body in the deployed position.

In at least some embodiments, one of the first and second attachment rings has a flared shape and is spaced apart from the lead body at one end. In at least some embodiments, the anchoring unit further includes a spring coupled to at least one of the first and second attachment rings and configured and arranged to bias the anchoring unit to the deployed position.

Any of the anchoring units described above can include any of the following additional features. In at least some embodiments, the first attachment ring includes an outer ring surface and at least one of the longitudinal struts includes a biasing portion attached to the first attachment ring and extending outwardly away from the outer ring surface of the first attachment ring and the lead body. In at least some embodiments, at least one of the longitudinal struts includes a thinner portion having a smaller lateral width than an adjacent portion of the longitudinal strut and attached to the first attachment ring, wherein the longitudinal strut preferentially bends at the thinner portion.

Any of the anchoring units described above can include any of the following additional features. In at least some embodiments, each of the longitudinal struts includes a longitudinal edge and serrations extending along the longitudinal edge. In at least some embodiments, each of the longitudinal struts includes two opposing longitudinal edges and serrations extending along each of the two opposing longitudinal edges. In at least some embodiments, each longitudinal strut of the anchoring unit is configured and arranged to form, in the deployed position, a corrugated region using the serrations.

Yet another embodiment is an electrical stimulation system that includes the electrical stimulation lead described above and a control module coupleable to the electrical stimulation lead.

A further embodiment is a method of implanting a lead. The method includes providing the electrical stimulation lead described above with at least a portion of the electrical stimulation lead, including the anchoring unit, disposed within an introducer with the anchoring unit the retracted position; inserting the introducer and electrical stimulation lead into patient tissue, withdrawing the introducer to expose the anchoring unit; and deploying the anchoring unit into the deployed state.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 11A is a schematic side view of an eighth embodiment of a lead anchoring unit with a flared attachment ring and in a deployed position on a portion of a lead, according to the invention;

FIG. 11B is a cross-sectional view of a portion of the lead anchoring unit and lead of FIG. 11A, according to the invention;

FIG. 11C is a schematic side view of two of the lead anchoring units of FIG. 11A on a portion of a lead, according to the invention;

DETAILED DESCRIPTION

The present invention is directed to the area of implantable electrical stimulation systems and methods of making and using the systems, and in particular implantable electrical stimulation leads having anchoring units with longitudinal struts and methods of making and using the leads.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
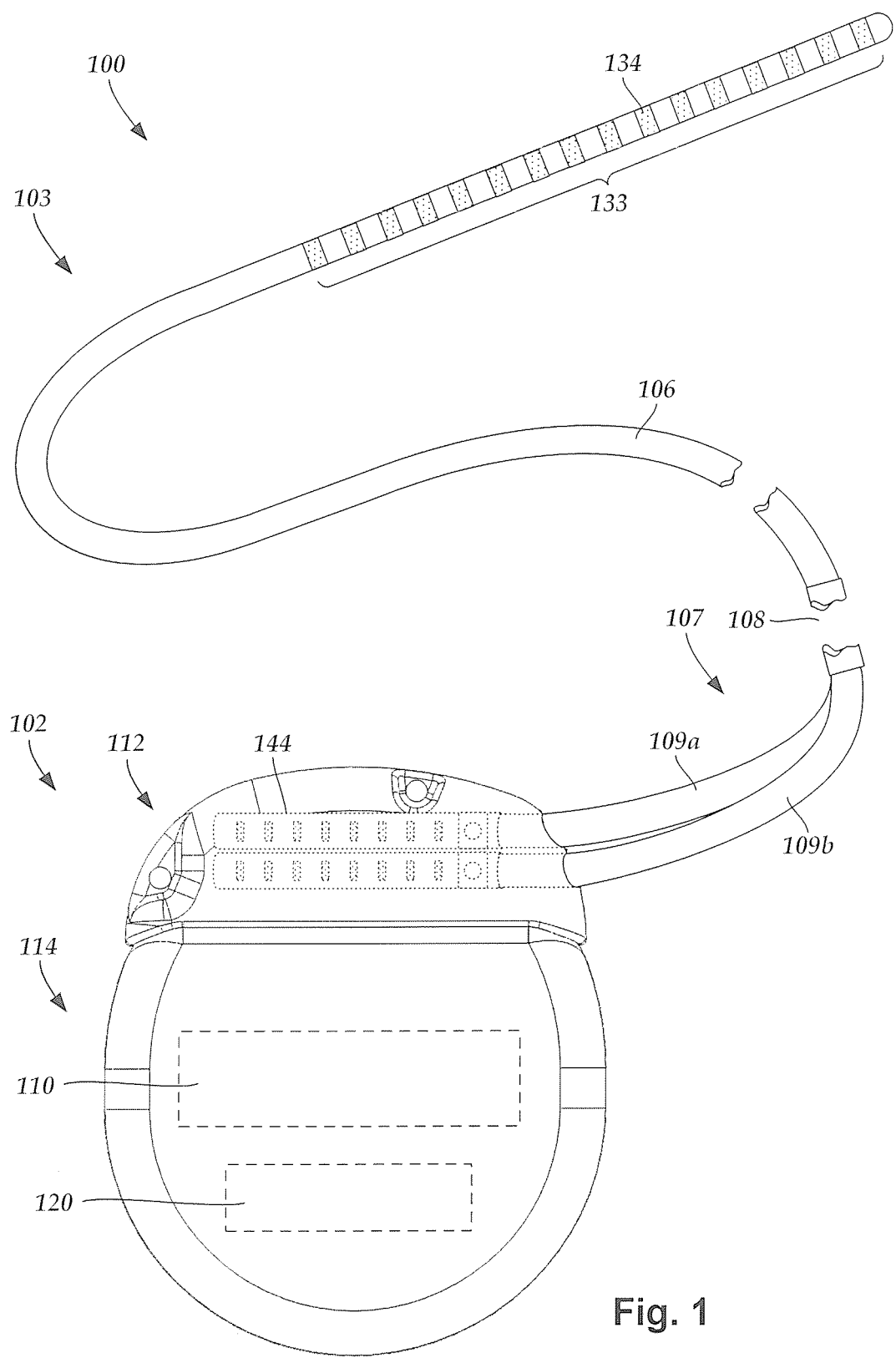
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIGS. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation; neural stimulation; spinal cord stimulation; muscle stimulation; neurostimulation to treat one or more of overactive bladder, urinary incontinence, fecal incontinence, or other bladder/bowel conditions; and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
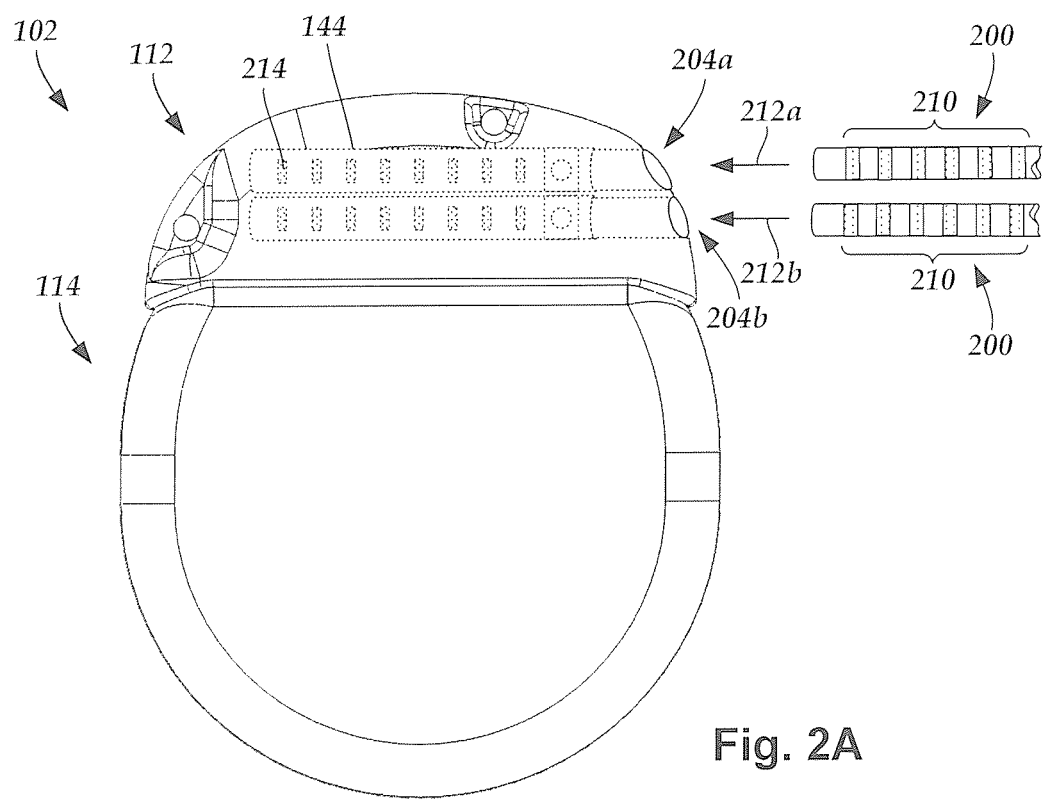
FIG. 2A is a schematic view of one embodiment of the control module of FIG. 1 configured and arranged to electrically couple to an elongated device, according to the invention.
Figure 2B:
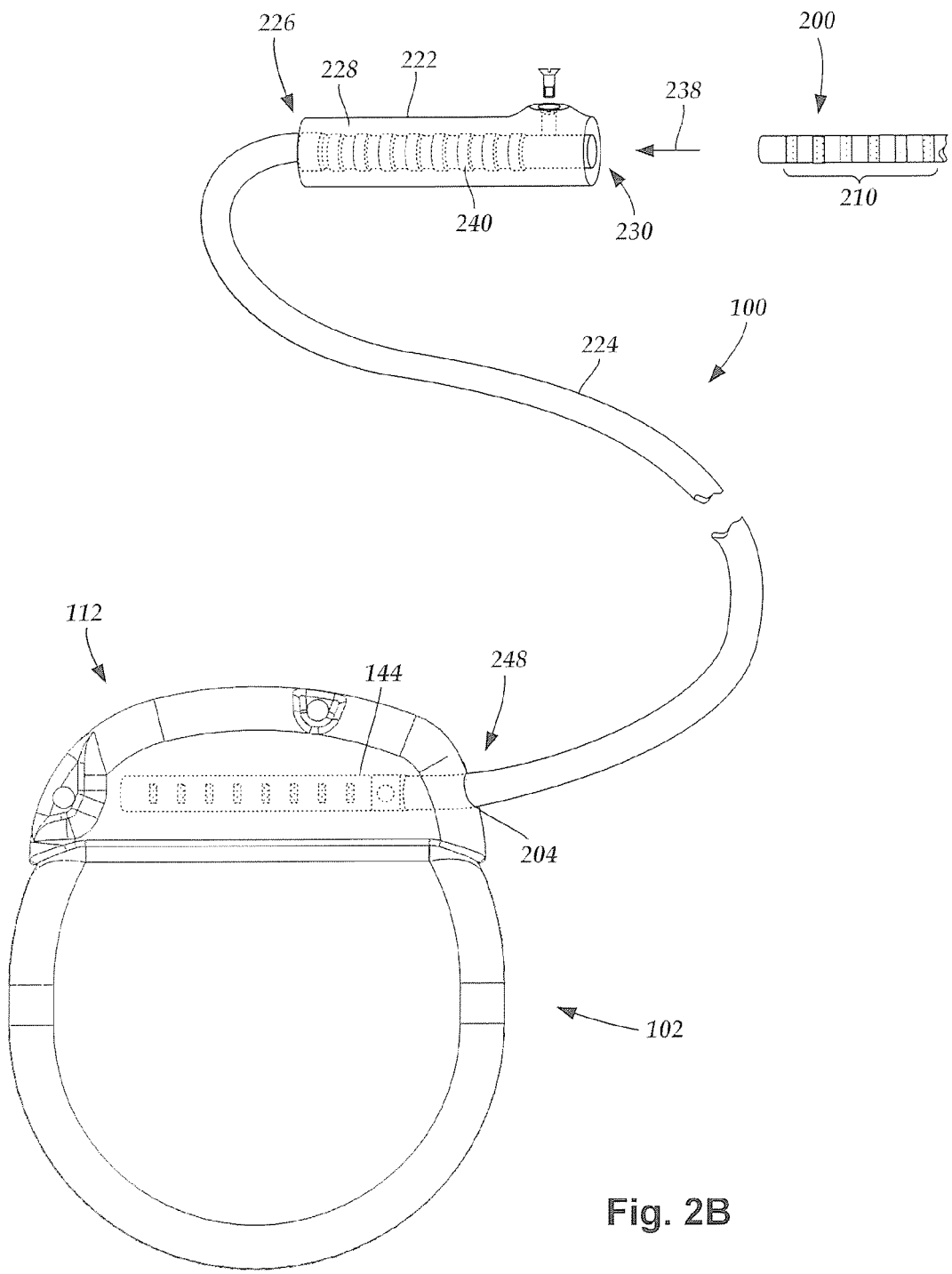
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIG. 2A and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Lead anchoring units can be attached to the lead to facilitate anchoring the lead into patient tissue. The term "tissue" includes, but is not limited to, muscular tissue, connective tissue, organ tissue, bone, cartilage, nerve tissue, and the like. These lead anchoring units, as opposed to conventional lead anchors, can be delivered with the lead through an introducer during the implantation process. The lead anchoring units include anchoring elements that lodge against patient tissue and prevent or reduce lateral or axial (or both lateral and axial) migration of the lead after implantation. The lead anchoring units can be particularly useful for leads for sacral nerve stimulation, spinal cord stimulation, or the stimulation of other patient tissue and organs.

Figure 3A:
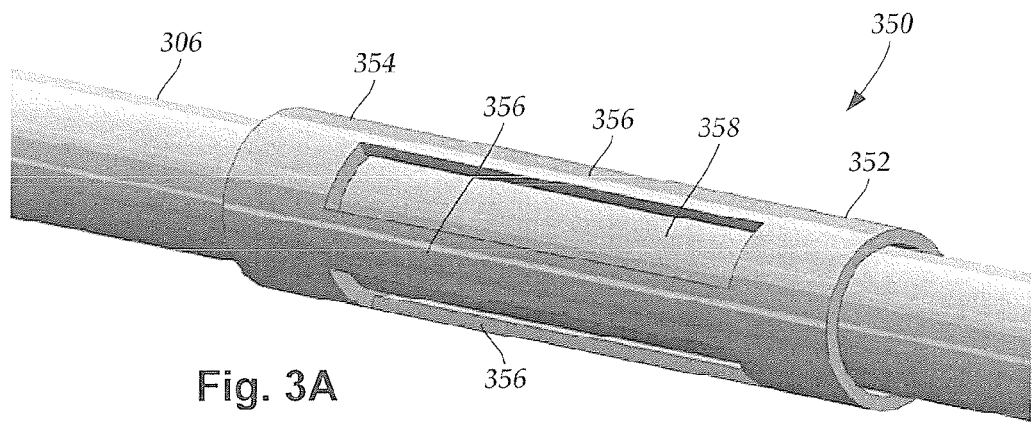
FIG. 3A is a schematic perspective view of one embodiment of a lead anchoring unit in a retracted position on a portion of a lead, according to the invention.
Figure 3B:
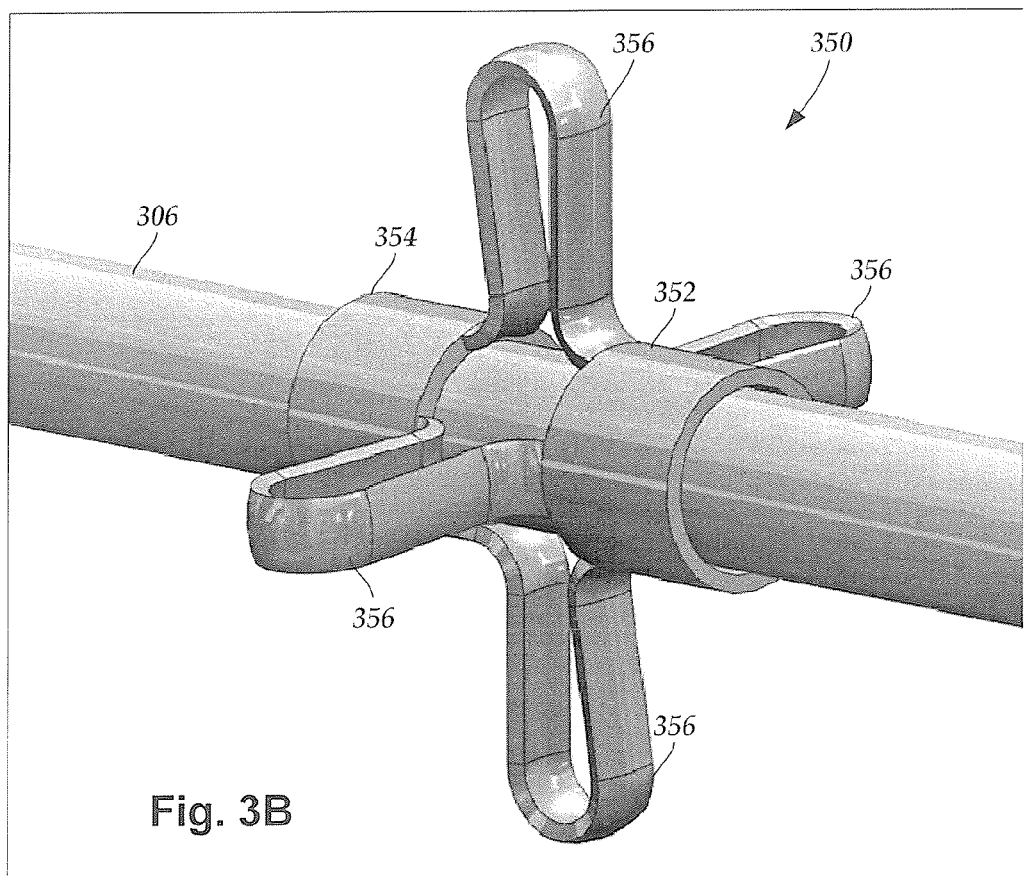
FIG. 3B is a schematic perspective view of the lead anchoring unit of FIG. 3A in a deployed position on a portion of a lead, according to the invention.

FIGS. 3A and 3B illustrate one embodiment of a lead anchoring unit 350 that can be disposed along a distal end portion of a lead body 306 (e.g., the lead body 106 as shown in FIG. 1). The lead anchoring unit facilitates anchoring the lead body to the surrounding tissue when implanted within a patient's body. The lead anchoring unit 350 can be disposed proximal to all of the electrodes (e.g., the electrodes 134 of FIG. 1.) In other embodiments, a lead anchoring unit 350 may be disposed between two electrodes or distal to all of the electrodes.

The anchoring unit 350 includes a first attachment ring 352, a second attachment ring 354, and multiple longitudinal struts 356 extending between the attachment rings with openings 358 between the longitudinal struts. The attachment rings 352, 354 can have a tube-shaped (e.g., cylindrical) configuration. As shown, the attachment rings 352, 354 define a central lumen extending along the length of the attachment ring. The central lumen fits around at least a portion of the lead body 306. In at least some embodiments, the attachment rings 352, 354 have a circular cross-section. In at least some embodiments, the cross-section and dimensions of the attachment rings 352, 354 are dictated by the configuration of the lead body.

In at least some embodiments, one of the attachment rings 352, 354 is slidable along the lead body. Optionally, the slidable attachment ring forms a friction fit with the lead body. The slidable attachment ring can be the attachment ring closest to the proximal end portion of the lead or the attachment ring closest to the distal end portion of the lead. The selection of which attachment ring is the slidable attachment ring may be determined by the mechanism for deploying the longitudinal struts, as described below. In some embodiments, both attachment rings may be slidable. In other embodiments, one of the attachment rings is fixed to the lead body by, for example, adhesive, welding to a metal ring, polymer reflow or welding between the attachment ring and the lead body, or the like.

In some embodiments, one or more stops, such as bumps, edges, protrusions, or the like may be formed on the lead body to halt or resist sliding of an attachment ring beyond the stop on the lead body. In some embodiments, a portion of the lead body may have a smaller outer diameter (formed, for example, by grinding, molding, cutting, ablation, or the like) so that the attachment ring can slide along the smaller-diameter portion of the lead body with the adjacent larger-diameter portions of the lead body acting as a stop to halt or resist sliding of the attachment ring. Such arrangements can be used with any of the anchoring units described herein.

The longitudinal struts 356 are disposed around the attachment rings 352, 354 with any regular or irregular spacing, corresponding to openings 358, between longitudinal struts. The longitudinal struts 356 extend preferably in a linear longitudinal arrangement with respect to the lead body 306. The anchoring unit 350 can have any suitable number of longitudinal struts 356 including, but not limited to, two, three, four, five, six, seven, eight, or more longitudinal struts.

The longitudinal struts 356 can have the same longitudinal length. The lateral or circumferential widths of the longitudinal struts 356 can be uniform or vary along the length of the individual longitudinal struts and may be the same or different between the individual longitudinal struts. The lateral or circumferential widths of the openings 358 between the longitudinal struts 356 can be uniform or vary along the length of the individual openings and may be the same or different between the individual openings.

FIG. 3A illustrates the anchoring unit 350 in a retracted position. In the retracted position, at least a portion of each of the longitudinal struts 356 lies next to the lead body and the longitudinal struts do not overlap each other. In some embodiments, the entire longitudinal strut lies next to the lead body in the retracted position. In other embodiments, only a portion of the longitudinal strut near one end, near both ends, or near the center of the longitudinal strut (or any combination thereof) lies next to the lead body in the retracted position.

The retracted position is useful for implantation by delivery of the lead, with one or more anchoring units 350 attached, through an introducer, such as a needle, sheath, or cannula or any other suitable introducer. When the lead is inserted into the introducer, the longitudinal struts 356 are in the retracted position to reduce the overall outer diameter of the arrangement of lead and anchoring unit(s) to no greater than the inner diameter of the introducer. When the lead is implanted, the introducer is removed allowing the longitudinal struts 356 to extend into a deployed position illustrated in FIG. 3B.

In the deployed position, the longitudinal struts 356 extend away from the lead body 306 while remaining coupled or attached to the attachment rings 342, 344. In some embodiments, the longitudinal struts 356 extend perpendicularly or near (within 5 or 10 degrees) perpendicularly with respect to the lead body 306 in the deployed position. In some embodiments, the longitudinal struts 356 may make any acute angle with respect to the lead body 306 (see, for example, FIGS. 6B and 7B). For example, the angle can be in the range of 25-90 degrees or 30-90 degrees or 45-90 degrees or 60-90 degrees or 30-75 degrees or 30-60 degrees or any other suitable range. In some embodiments, the longitudinal struts are angled toward the proximal end portion of the lead to resist proximal movement of the lead. In some embodiments, the longitudinal struts are angled toward the distal end portion of the lead to resist distal movement of the lead. The longitudinal struts 356 can be deployed at the same angle with respect to the lead body 306 or at different angles. The deployment angle of the longitudinal struts 356 may depend on the method or degree of deployment.

In the illustrated embodiment, the longitudinal struts 356 each form a narrow, partial loop which may facilitate tissue in-growth within the partial loop to further anchor the lead to the patient tissue. In other embodiments, the longitudinal struts may form a bulge-like structure (see, for example, FIG. 8B). The structure that is obtained may depend on the degree to which the attachment rings are brought together and may or may not be selectable by the user that deploys the anchoring unit. When implanted, the longitudinal struts 356 extend into tissue to anchor the lead to the tissue. When deployed, the longitudinal struts 356 can be rigid or can have a degree of flexibility to prevent or reduce damage to surrounding tissue.

In at least some embodiments, the longitudinal struts 356 are arranged to preferentially extend in the deployed position unless constrained by, for example, the introducer. For example, the anchoring unit 350 may be heat treated in the deployed position to make the deployed position preferential. In some embodiments, the longitudinal struts 356 may be deployed into the deployed position, after withdrawal of the introducer, by pushing one or both of the attachment rings 342, 344 toward each other using, for example, the introducer or a deployment tool; pulling the lead backward; pushing the lead forward; or any combination of these movements or any other suitable movement (or combination of movements) of the lead or anchoring unit. In some embodiments, the tissue within which the lead is implanted can aid in deployment as the lead is pushed or pulled with the tissue acting as a force against one of the attachment rings to resist movement of the attachment ring with the lead causing the attachment ring to slide relative to the lead. Alternatively, other methods or mechanisms for deploying the longitudinal struts 356 can also be used. It will be understood that these anchoring unit configurations, arrangements, and methods of deployment can be used with any of the anchoring units described herein.

Figure 4:
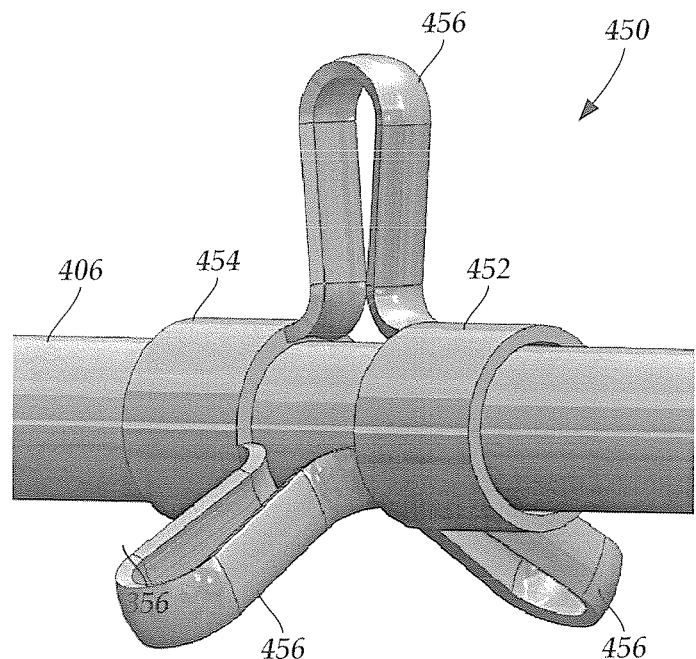
FIG. 4 is a schematic perspective view of a second embodiment of a lead anchoring unit in a deployed position on a portion of a lead, according to the invention.

FIG. 4 illustrates another embodiment of an anchoring unit 450 disposed on a lead body 406 in the deployed position. The anchoring unit 450 includes a first attachment ring 452, a second attachment ring 454, and three longitudinal struts 456. All of these elements, and the design considerations for these elements, are the same as the corresponding (similarly named) elements of the embodiment illustrated in FIGS. 3A and 3B.

Figure 5:
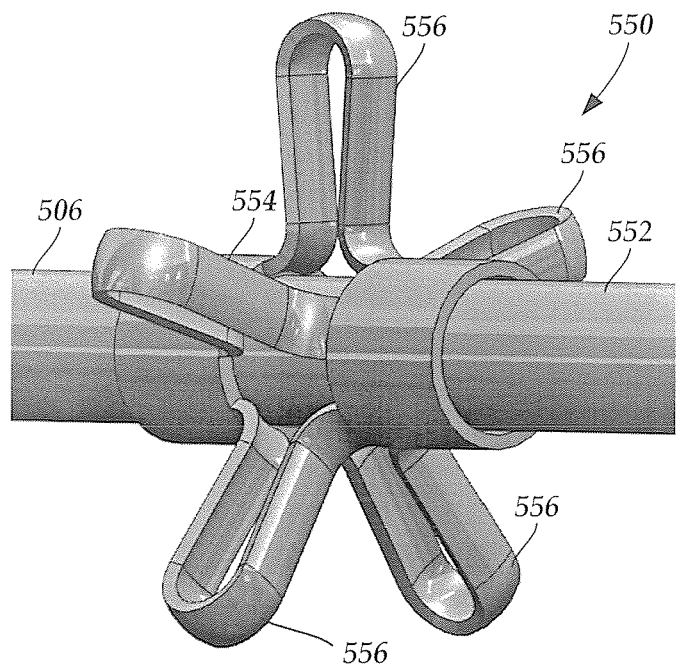
FIG. 5 is a schematic perspective view of a third embodiment of a lead anchoring unit in a deployed position on a portion of a lead, according to the invention.

FIG. 5 illustrates another embodiment of an anchoring unit 550 disposed on a lead body 506 in the deployed position. The anchoring unit 550 includes a first attachment ring 552, a second attachment ring 554, and five longitudinal struts 556. All of these elements, and the design considerations for these elements, are the same as the corresponding (similarly named) elements of the embodiment illustrated in FIGS. 3A and 3B.

Figure 6A:
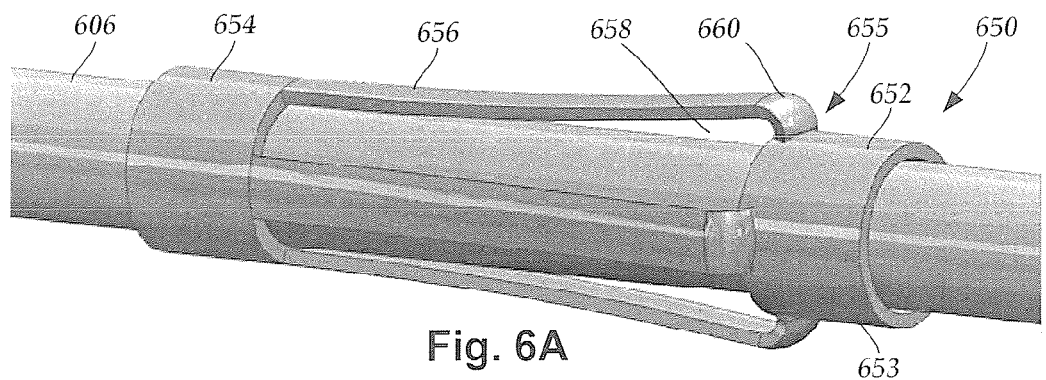
FIG. 6A is a schematic perspective view of a fourth embodiment of a lead anchoring unit in a retracted position on a portion of a lead, according to the invention.
Figure 6B:
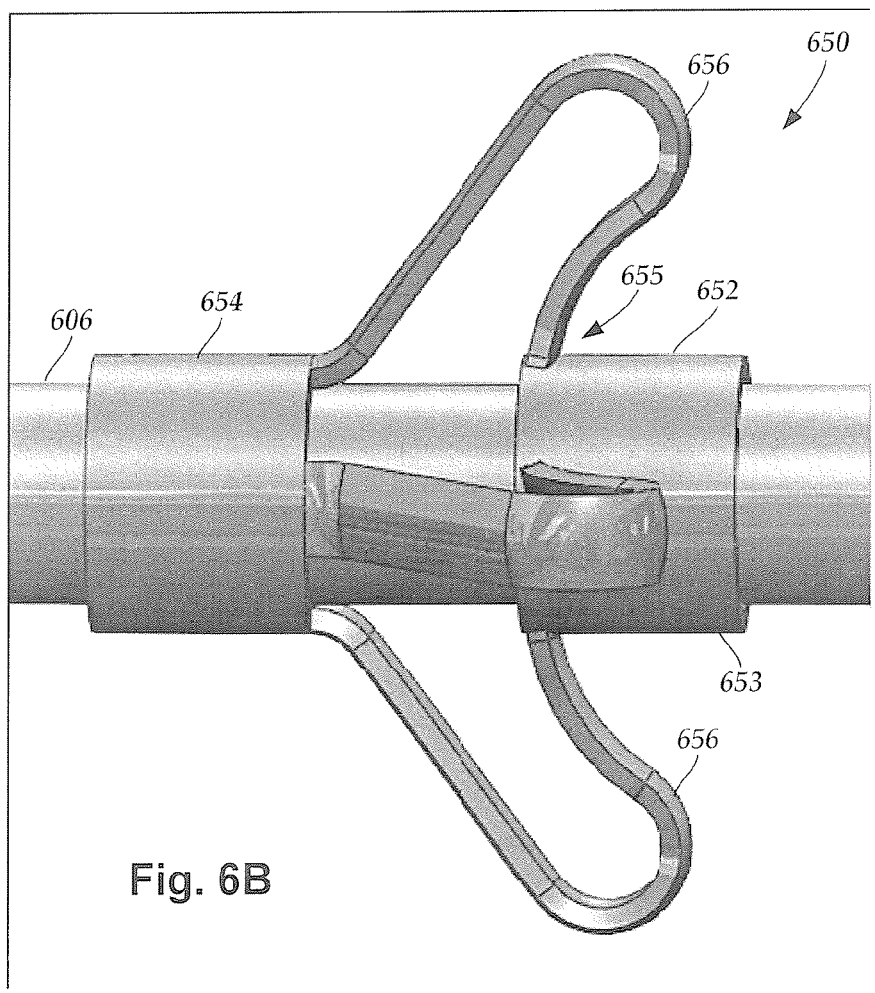
FIG. 6B is a schematic perspective view of the lead anchoring unit of FIG. 6A in a deployed position on a portion of a lead, according to the invention.

FIGS. 6A and 6B illustrate another embodiment of an anchoring unit 650 disposed on a lead body 606 in the retracted position (FIG. 6A) and the deployed position (FIG. 6B). The anchoring unit 650 includes a first attachment ring 652, a second attachment ring 654, four longitudinal struts 656, and openings 658. All of these elements, and the design considerations for these elements, are the same as the corresponding (similarly named) elements of the embodiment illustrated in FIGS. 3A and 3B, unless indicated otherwise.

The longitudinal struts 656 in this embodiment include a biasing portion 660 which extends outwardly away from an outer ring surface 653 of the first attachment ring 652 and the lead body 606 even in the retracted position, as illustrated in FIG. 6A. In at least some embodiments, the biasing portion 660 of the longitudinal strut 656 does not lie next to the lead body 606 in the retracted position, nor does part of the longitudinal strut adjacent the biasing portion, as illustrated in FIG. 6A. The biasing portion 660 forms an angle 655 with the outer ring surface 653 that is less than 180 degrees, 150 degrees or less, 135 degrees or less, 120 degrees or less, or 90 degrees or less.

The biasing portion 660 facilitates biasing the longitudinal strut to angle towards first attachment ring 652 in the deployed position, as illustrated in FIG. 6B, instead of the longitudinal strut extending perpendicularly (as illustrated in FIG. 3B). If the first attachment ring 652 is disposed on the lead body 606 proximal to the second attachment ring 654, then the longitudinal struts 656 in the illustrated embodiment will be angled toward the proximal end portion of the lead. If the first attachment ring 652 is disposed on the lead body 606 distal to the second attachment ring 654, then the longitudinal struts 656 in the illustrated embodiment will be angled toward the distal end portion of the lead. It will be understood that a biasing portion can be added to the longitudinal strut(s) of any of the other anchoring units described herein.

In the illustrated embodiment, all of the longitudinal struts 656 have a biasing portion 660 coupled or attached to the first attachment ring 652. In other embodiments, some, but less than all, of the longitudinal struts 656 have a biasing portion 660. The other longitudinal struts can be coupled to the attachment rings 652, 654 in the same configuration illustrated in FIG. 3A. The selection of which longitudinal struts 656 have a biasing portion may be random, in an irregular pattern, or in a regular pattern (for example, every other longitudinal strut, every third longitudinal strut, etc, or longitudinal struts on opposite sides of the lead body, or the like).

In some embodiments, one or more longitudinal struts 656 (i.e., first longitudinal strut(s)) have a biasing portion 660 coupled or attached to the first attachment ring 652 and one or more of the other longitudinal struts (i.e., second longitudinal strut(s)) having a biasing portion 660 coupled or attached to the second attachment ring 654. Optionally, there may be further longitudinal struts (i.e., third longitudinal strut(s)) that have no biasing portion. The selection of which longitudinal struts are first longitudinal struts, second longitudinal struts, or optional third longitudinal struts may be random, in an irregular pattern, or in a regular pattern (for example, alternating first and second longitudinal struts, or alternating first, second, and third longitudinal struts, or the like).

Figure 7A:
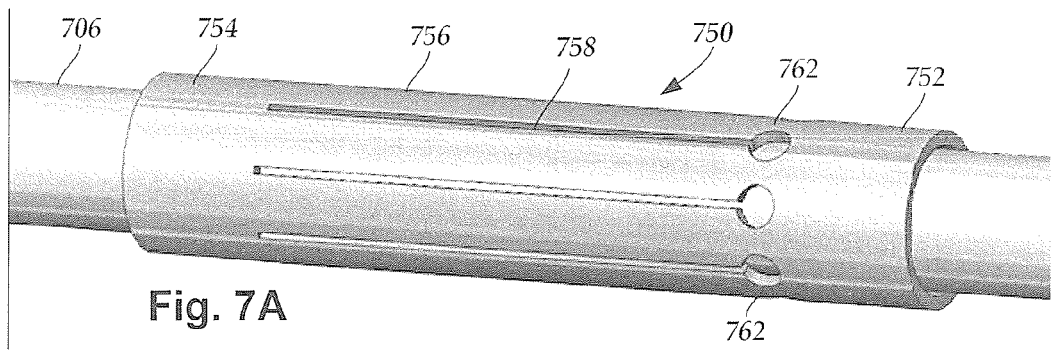
FIG. 7A is a schematic perspective view of a fifth embodiment of a lead anchoring unit in a retracted position on a portion of a lead, according to the invention.
Figure 7B:
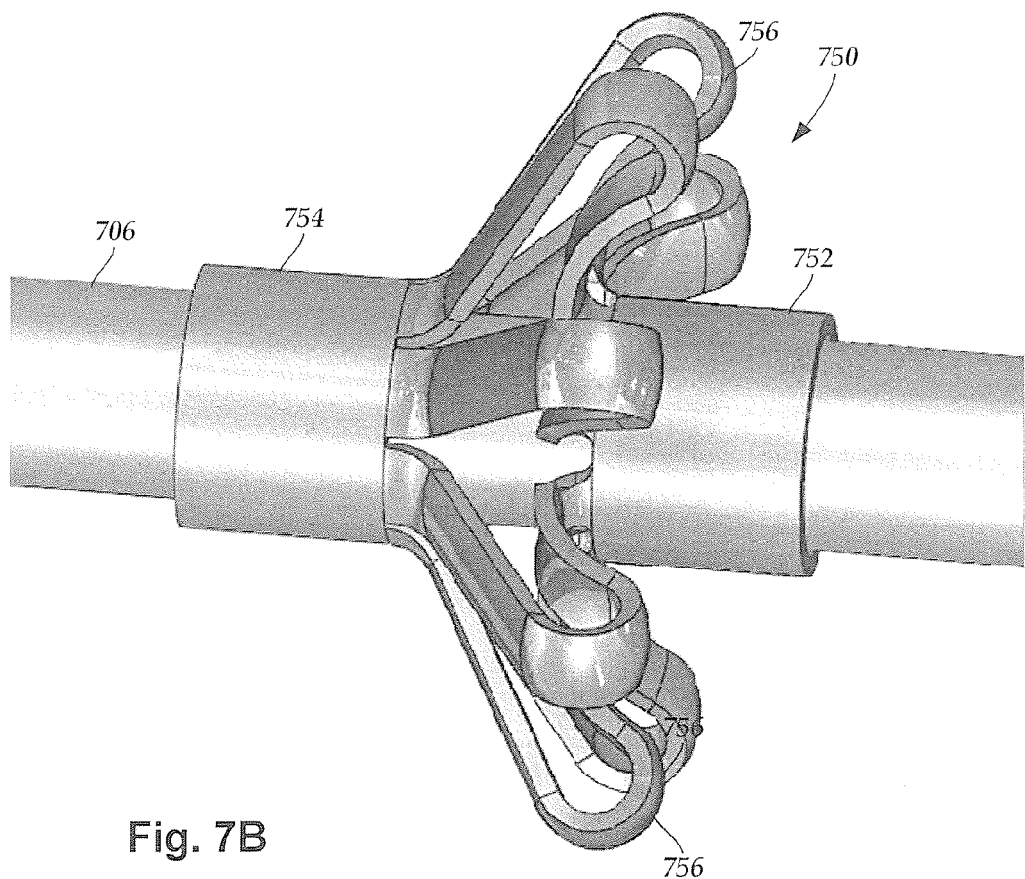
FIG. 7B is a schematic perspective view of the lead anchoring unit of FIG. 7A in a deployed position on a portion of a lead, according to the invention.

FIGS. 7A and 7B illustrate another embodiment of an anchoring unit 750 disposed on a lead body 706 in the retracted position (FIG. 7A) and the deployed position (FIG. 7B). The anchoring unit 750 includes a first attachment ring 752, a second attachment ring 754, eight longitudinal struts 756, and openings 758. All of these elements, and the design considerations for these elements, are the same as the corresponding (similarly named) elements of the embodiment illustrated in FIGS. 3A and 3B, unless indicated otherwise.

The longitudinal struts 756 in this embodiment include a thinner portion 762 where the longitudinal strut attaches to the first attachment ring 752, as illustrated in FIG. 7A. The thinner portion 762 preferentially bends so that the longitudinal strut, in the deployed position bends at an angle toward the thinner portion 762, as illustrated in FIG. 7B, instead of the longitudinal strut extending perpendicularly (as illustrated in FIG. 3B). If the first attachment ring 752 is disposed on the lead body 706 proximal to the second attachment ring 754, then the longitudinal struts 756 in the illustrated embodiment will be angled toward the proximal end portion of the lead. If the first attachment ring 752 is disposed on the lead body 706 distal to the second attachment ring 754, then the longitudinal struts 756 in the illustrated embodiment will be angled toward the distal end portion of the lead. It will be understood that a thinner portion can be added to the longitudinal strut(s) of any of the other anchoring units described herein.

In the illustrated embodiment, all of the longitudinal struts 756 have a thinner portion 762 where the longitudinal strut attaches to the first attachment ring 752. In other embodiments, some, but less than all, of the longitudinal struts 756 have a thinner portion 762. The other longitudinal struts can be coupled to the attachment rings 752, 754 in the same configuration illustrated in FIG. 3A. The selection of which longitudinal struts 756 have a thinner portion may be random, in an irregular pattern, or in a regular pattern (for example, every other longitudinal strut, every third longitudinal strut, etc. or longitudinal struts on opposite sides of the lead body, or the like).

In some embodiments, one or more longitudinal struts 756 (i.e., first longitudinal strut(s)) have a thinner portion 762 where the longitudinal strut attaches to the first attachment ring 752 and one or more of the other longitudinal struts (i.e., second longitudinal strut(s) having a thinner portion 762 where the longitudinal strut attaches to the second attachment ring 754. Optionally, there may be further longitudinal struts (i.e., third longitudinal strut(s)) that have no thinner portion. The selection of which longitudinal struts are first longitudinal struts, second longitudinal struts, or optional third longitudinal struts may be random, in an irregular pattern, or in a regular pattern (for example, alternating first and second longitudinal struts, or alternating first, second, and third longitudinal struts, or the like).

Figure 8A:
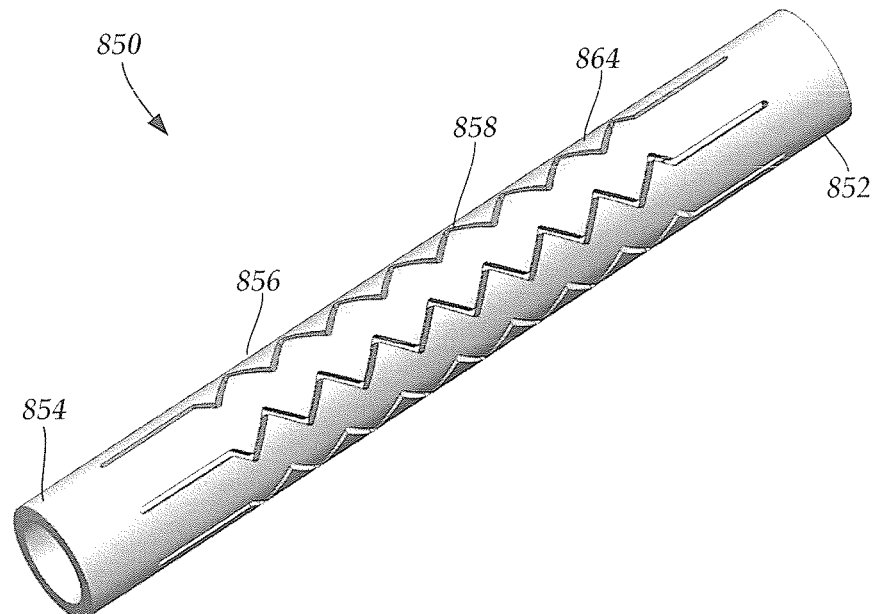
FIG. 8A is a schematic perspective view of a sixth embodiment of a lead anchoring unit in a retracted position on a portion of a lead, according to the invention.
Figure 8B:
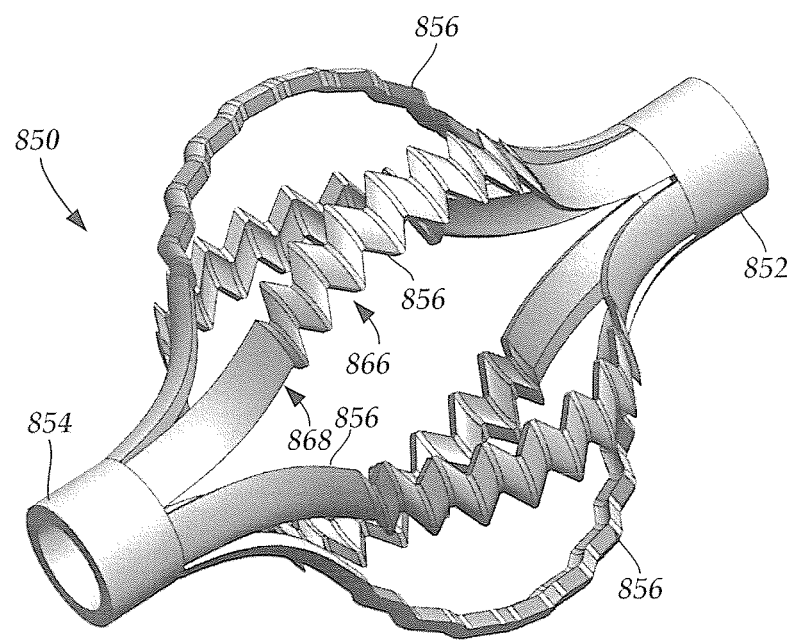
FIG. 8B is a schematic perspective view of the lead anchoring unit of FIG. 8A in a deployed position on a portion of a lead, according to the invention.

FIGS. 8A and 8B illustrate another embodiment of an anchoring unit 850 disposed on a lead body 806 in the retracted position (FIG. 8A) and the deployed position (FIG. 8B). The anchoring unit 850 includes a first attachment ring 852, a second attachment ring 854, six longitudinal struts 856, and openings 858. All of these elements, and the design considerations for these elements, are the same as the corresponding (similarly named) elements of the embodiment illustrated in FIGS. 3A and 3B, unless indicated otherwise.

In the embodiment of FIGS. 8A and 8B, the longitudinal struts 856 and corresponding openings 858 are serrated to form a series of peaks and valleys along the edges of the longitudinal struts and openings. Any suitable number of serrations 864 can be included along the longitudinal strut. The pitch between serrations, as well as the width, angle, and depth of the serrations, can be uniform or non-uniform along the length of the longitudinal strut 856 and can be the same or different on the two edges of the longitudinal strut and can be the same or different for different struts. It will be understood that serrations can be added to the longitudinal strut(s) of any of the other anchoring units described herein.

The serrations 864 on the edges of the longitudinal strut can extend the full length of the longitudinal strut 856 or only part of the length, for example, no more than 90%, 80%, 75%, 50%, or 25% of the length of the longitudinal strut 856. If the serrations extend for less than the full length of the longitudinal strut, a non-serrated region 868 (FIG. 8B) of the longitudinal strut may be positioned adjacent the first attachment ring, adjacent the second attachment ring, at the center of the longitudinal strut, or any combination of these positions or at any other position along the longitudinal strut. In the illustrated embodiment, the longitudinal strut 856 includes non-serrated portions near both the first and second attachment rings 852, 854.

In the deployed position, the serrated portion of the longitudinal struts 856 may form a corrugated, or accordion-like, region 866, as illustrated in FIG. 8B. These serrations 864 form additional surfaces for the anchoring unit 850 to engage, grip, or grab tissue. These additional surfaces may also enhance tissue in-growth. The serrations 864 (and corresponding longitudinal struts 856 and openings 858) can be formed by molding, injection molding, extrusion, casting, laser cutting, die cutting, and the like.

In the illustrated embodiment, all of the longitudinal struts 856 have serrations 864. In other embodiments, some, but less than all, of the longitudinal struts 856 (i.e., first longitudinal struts) have serrations 864. The other longitudinal struts (i.e., second longitudinal struts) can have straight edges as illustrated in FIG. 3A. The selection of which longitudinal struts 856 have serrations may be random, in an irregular pattern, or in a regular pattern (for example, every other longitudinal strut, every third longitudinal strut, etc. or longitudinal struts on opposite sides of the lead body, or the like).

In addition, the illustrated embodiment shows serrations 864 on both longitudinal edges of the longitudinal strut 856. It will be understood that, in other embodiments, any longitudinal strut can have serrations on only one longitudinal edge or the serrations on the longitudinal edges may occupy different portions of the longitudinal length of the longitudinal strut.

Figure 9A:
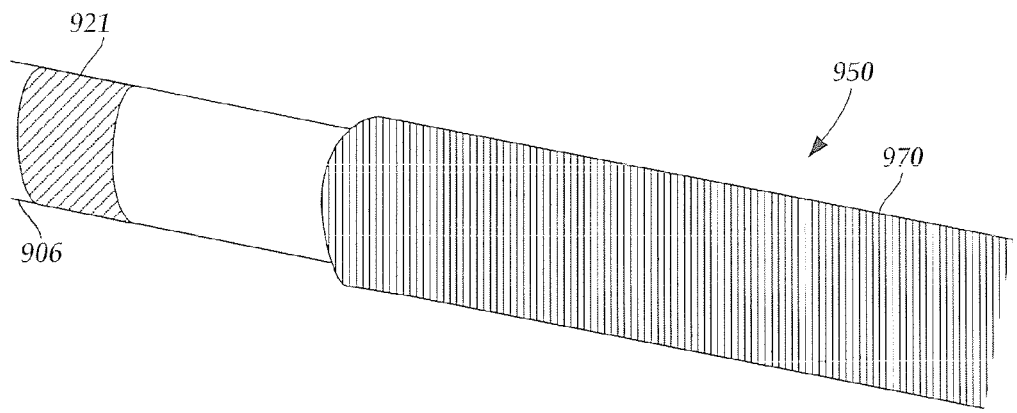
FIG. 9A is a schematic perspective view of a proximal portion of a seventh embodiment of a lead anchoring unit in a retracted position on a portion of a lead, according to the invention.
Figure 9B:
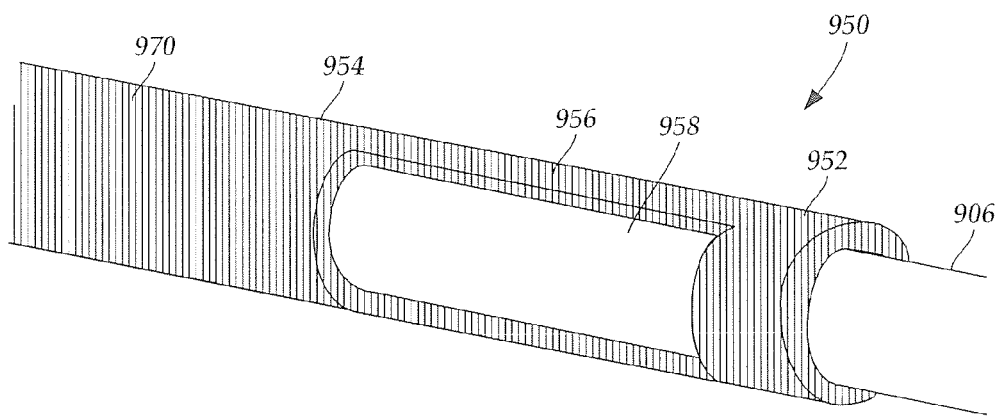
FIG. 9B is a schematic perspective view of a distal portion of the lead anchoring unit of FIG. 9A in the retracted position on a portion of a lead, according to the invention.

FIGS. 9A and 9B illustrate another embodiment of an anchoring unit 950 disposed on a lead body 906 in the retracted position. FIG. 9A illustrates a portion of the lead at the proximal end of the anchoring unit 950 near the terminals 921 of the lead and FIG. 9B illustrates a portion of the lead at the distal end of the anchoring unit 950. The anchoring unit 950 includes a first attachment ring 952, a second attachment ring 954, longitudinal struts 956, and openings 958. All of these elements, and the design considerations for these elements, are the same as the corresponding (similarly named) elements of the embodiment illustrated in FIGS. 3A and 3B, unless indicated otherwise.

In the embodiment of FIGS. 9A and 9B, the anchoring unit 950 extends proximally to near the proximal end (see, FIG. 9A) of the lead terminating prior to the terminals 921 by including an extension portion 970. The extension portion 970 of the anchoring unit 950 is an extension of one of the attachment rings (for example, the second attachment ring 954 in FIG. 9B). The deployed position of anchoring unit 950 is similar to that of anchoring unit 350 except that the extension portion 970 extends proximally from the second attachment ring. It will be understood that an extension portion 970 can be incorporated in any of the other anchoring units described herein.

The extension portion 970 permits a user to manually adjust the anchoring unit 950 between the retracted position and the deployed position by pushing or pulling the proximal end of the extension portion 970 of the anchoring unit 950. In some embodiments, the anchoring unit 950 may preferentially extend in the deployed position unless constrained by, for example, the introducer. The extension portion 970 is provided to allow manual adjustment to the retracted position or as a safeguard if the anchoring unit does not deploy or does not deploy by the desired amount.

The extension portion 970 can be formed integrally (i.e., in one piece) with the remainder of the anchoring unit 950 or it can be attached to one of the attachment rings by adhesive, welding, or the like or it can simply abut one of the attachment rings.

Figure 9C:
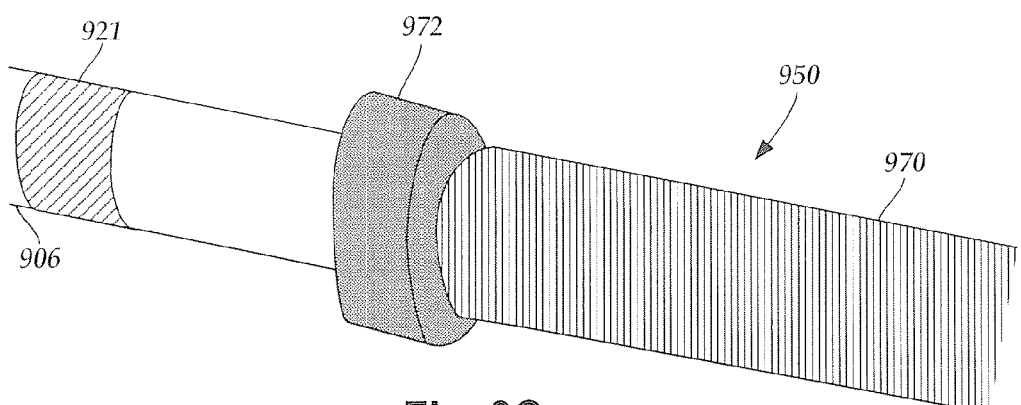
FIG. 9C is a schematic perspective view of the proximal portion of the lead anchoring unit of FIG. 9A in a deployed position on a portion of a lead and with an optional holding unit, according to the invention.

In some embodiments, an optional holding unit 972 can be attached to the lead, proximal to the extension portion 970, or to the extension portion 970 after deployment of the longitudinal struts 956 to hold the anchoring unit 950 in the deployed position, as illustrated in FIG. 9C (compare to FIG. 9A). The holding unit 972 can be any device that grips the lead or anchoring unit to prevent or reduce the likelihood of movement of the anchoring unit back to the retracted position. Alternatively or additionally, the lead body 906 and anchoring unit 950 may have cooperating locking elements (e.g., one or more bumps, grooves, or the like and corresponding protrusions) that engage when the anchoring unit 950 is pushed into the deployed position to hold the anchoring unit 950 in the deployed position.

FIG. 11A illustrates another embodiment of an anchoring unit 1150 disposed on a lead body 1106 in the deployed position. The anchoring unit 1150 includes a first attachment ring 1152, a second attachment ring 1154, four longitudinal struts 1156, and openings 1158. All of these elements, and the design considerations for these elements, are the same as the corresponding (similarly named) elements of the embodiment illustrated in FIGS. 3A and 3B, unless indicated otherwise.

The second attachment ring 1154 in this embodiment has a flared shape that is open, and separated from the lead body 1106 as illustrated in FIG. 11B, at the end 1153 of the second attachment ring opposite the longitudinal struts 1156. This flared shape can be, for example, a cone shape or any other shape with larger outer diameter of the second attachment ring at one end 1153 than at the other end 1155. In the illustrated embodiment, the longitudinal struts 1156 are biased (e.g., directed) away from the flared second attachment ring 1154. In other embodiments, the longitudinal struts can be biased toward the flared second attachment or not biased with respect the flared second attachment ring. In yet other embodiments, any combination of biasing toward, biasing away from, or non-biased (with respect to the second attachment ring) longitudinal struts can be used.

In some embodiments, the second attachment ring may include ridges along the wall of the second attachment ring 1154 or at least one stiffening agent within or on the second attachment ring (or any combination of ridges and stiffening agents) to strengthen the second attachment ring against collapse. Alternatively or additionally, one or more slots, grooves, or slits in the wall of the second attachment ring 1154 can allow the ring to collapse easier, for example, for implantation through an introducer.

The flared shape of the second attachment ring 1154 can enhance the ease of deployment of the anchoring unit 1150 from the retracted position to the deployed position. The flared shape of the second attachment ring 1154 can also enhance the anchoring force of the anchoring unit 1150 within the tissue due, for example, to the larger cross-sectional area of the second attachment ring at the end 1153 or the open space between the second attachment ring and lead body 1106. Additionally or alternatively, the flared shape of the second attachment ring 1154 may also enhance tissue ingrowth into the space between the second attachment ring 1154 and the lead body 1106 to enhance anchoring of the lead over time. The size (e.g., largest outer diameter of the second attachment ring 1154) and stiffness (based on, for example, using selected materials; the presence of ridges, grooves, slots, slits, or stiffening elements within, or on, the second attachment ring; or the like; or any combination thereof) of the second attachment ring can be selected.

In the illustrated embodiment, the second attachment ring 1154 has a flared shape. It will be recognized, however, that alternatively or additionally, the first attachment ring 1152 can have a flared shape, separated from the lead body 1106, at the end of the first attachment ring opposite the longitudinal struts 1156. In addition, more than one anchoring unit 1050 can be used with a lead as illustrated in FIG. 11C where two anchoring units 1050 are presented on lead body 1106.

Figure 12:
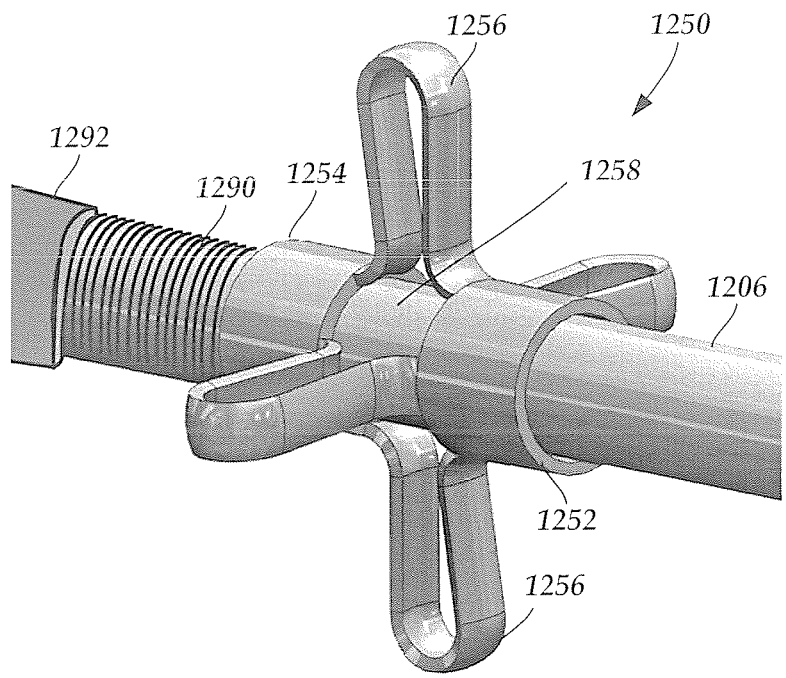
FIG. 12 is a schematic side view of a ninth embodiment of a lead anchoring unit with a spring and in a deployed position on a portion of a lead, according to the invention.

FIG. 12 illustrates another embodiment of an anchoring unit 1250 disposed on a lead body 1206 in the deployed position. The anchoring unit 1250 includes a first attachment ring 1252, a second attachment ring 1254, four longitudinal struts 1256, and openings 1258. All of these elements, and the design considerations for these elements, are the same as the corresponding (similarly named) elements of the embodiment illustrated in FIGS. 3A and 3B, unless indicated otherwise. In addition, the anchoring unit includes a spring 1290 and a biasing element 1292 coupled to the lead body 1206.

When moving to the retracted position, a retraction force is applied to the anchoring unit 1256 causing the longitudinal struts 1256 to be pushed downwards separating the first and second attachment rings 1252, 1254. The second attachment ring 1254 is slidable relative to the lead body 1206 and, therefore, the second attachment ring 1254 moves toward the biasing element 1292 compressing the spring 1290 from a deployed state (often where little or no force is exerted to compress the spring) to a higher energy compressed state. When the retraction force is removed, the spring 1290 expands to the deployed state causing the second attachment ring 1254 to move towards the first attachment ring 1252 to deploy the longitudinal struts 1256. In some embodiments, the spring 1290 may be covered by a tube or other material disposed over the spring 1290 and lead body to protect the spring from tissue and fluids.

Figure 13:
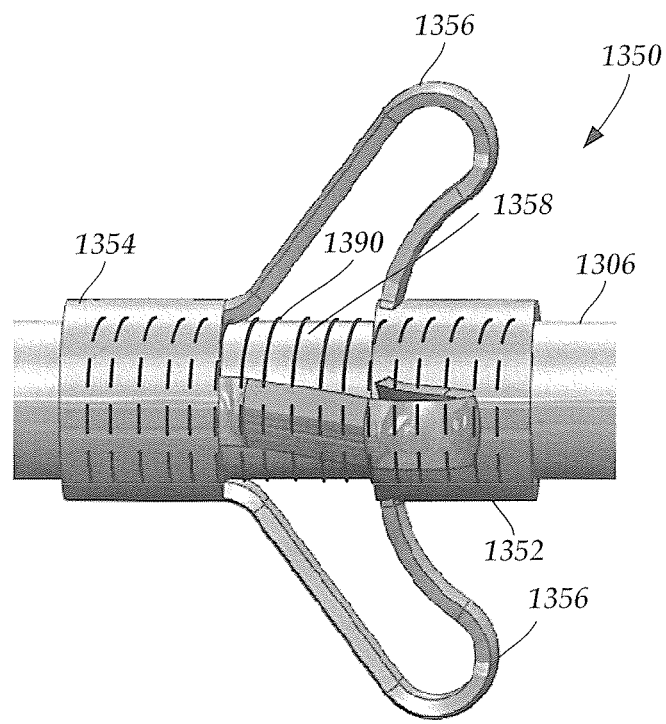
FIG. 13 is a schematic side view of a tenth embodiment of a lead anchoring unit with a spring and in a deployed position on a portion of a lead, according to the invention.

FIG. 13 illustrates another embodiment of an anchoring unit 1350 disposed on a lead body 1306 in the deployed position. The anchoring unit 1350 includes a first attachment ring 1352, a second attachment ring 1354, four longitudinal struts 1356, and openings 1358. All of these elements, and the design considerations for these elements, are the same as the corresponding (similarly named) elements of the embodiment illustrated in FIGS. 3A and 3B, unless indicated otherwise. In addition, the anchoring unit includes a spring 1390 coupled to the first and second attachment rings 1352, 1354.

When moving to the retracted position, a retraction force is applied to the anchoring unit 1356 causing the longitudinal struts 1356 to be pushed downwards separating the first and second attachment rings 1352, 1354. One of the first and second attachment rings 1352, 1354 is slidable relative to the lead body 1306 and as the first and second attachment rings separate, the spring 1390 expands from a deployed state (often where little or no force is exerted to compress the spring) to a higher energy expanded state. When the retraction force is removed, the spring 1390 compresses to the deployed state causing the first and second attachment rings 1352, 1354 to become closer and deploy the longitudinal struts 1356. In some embodiments, a portion of the spring 1390 between the first and second attachment rings 1352, 1354 may be covered by a tube or other material disposed over the spring 1390 and lead body to protect the spring from tissue and fluids.

In the embodiments of FIGS. 12 and 13, the spring 1290, 1390 can be made of metal, plastic, or any other spring-like material. The spring 1290, 1390 is depicted as a coil spring, but any other suitable spring (or set of springs), such as a leaf spring, can be used.

Any number of anchoring units can be used with a lead and any combination of the different anchoring units described above can be used. For example, a lead can have one, two, three, four, or more anchoring units. In some embodiments, all of the anchoring units are disposed proximal to all of the electrodes. In some embodiments, one or more anchoring units are positioned between the electrodes. In some embodiments, one or more of the anchoring units are disposed distal to all of the electrodes. For leads with multiple anchoring units, any combination of anchoring unit positions (distal to all electrodes, between electrodes, or proximal to all electrodes) can be used.

Any of the anchoring units described herein can be formed of any suitable material including, for example, polymer, metal, or alloy materials. Examples of suitable materials include, but are not limited to, polyurethane, silicone, Nitinol™, or the like or any combination thereof. In at least some embodiments, the anchoring unit is formed of silicone, polyurethane, or the like. In some embodiments, the material that is used has a stiffness that is sufficient to anchor the lead body to the surrounding tissue, while also having sufficient flexibility to reduce, or in some cases avoid, damage or injury to the tissue or to facilitate delivery of the lead with the anchoring unit(s) through an introducer.

Any of the anchoring units can be formed by any suitable manufacturing method including, but not limited to, molding, injection molding, extrusion, laser cutting, casting, or the like. The longitudinal struts and corresponding openings can be formed by molding, injection molding, extrusion, or casting or may be generated by the laser cutting, die cutting, or the like of a cylinder, sheet (which can be rolled to form a cylinder or other object), or other solid-surface object to form the longitudinal struts and openings.

Figure 10:
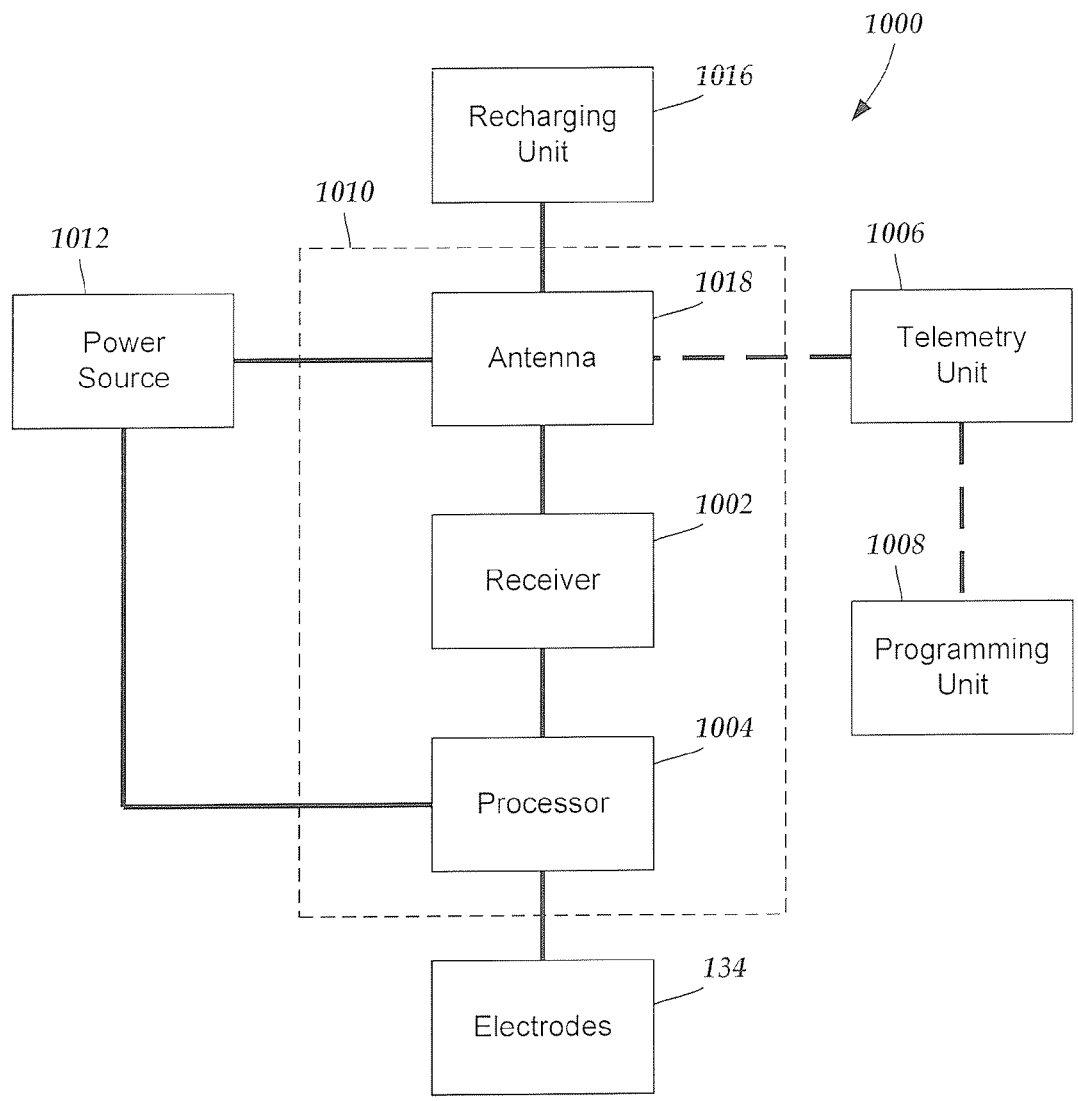
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, a power source 1012, an antenna 1018, a receiver 1002, and a processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 selects which electrode(s) are cathodes and which electrode(s) are anodes. In some embodiments, the processor 1004 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by the programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and the receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include the antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification provides a description of the manufacture and use of the invention. Since many embodiments of the invention can be made without departing from the scope of the invention, the invention also resides in the claims hereinafter appended.

What is claimed as new and desired to be protected by Letters Patent of the United States is:

1. An electrical stimulation lead, comprising:
   a lead body having a distal end portion and a proximal end portion;
   a plurality of electrodes disposed along the distal end portion of the lead body;
   a plurality of terminals disposed along the proximal end portion of the lead body;
   a plurality of conductors disposed within the lead body, each conductor of the plurality of conductors electrically coupling each of the plurality of terminals to at least one of the plurality of electrodes; and
   an anchoring unit disposed along the distal end portion of the lead body, the anchoring unit having a first end and a second end and comprising
      a first attachment ring disposed at the first end,
      a second attachment ring disposed at the second end, wherein one of the first attachment ring or second attachment ring is fixed to the lead body and another one of the first attachment ring and the second attachment ring is slidably engaged around the lead body, and
      a plurality of longitudinal struts extending linearly between, and coupled to, the first and second attachment rings, wherein at least a portion of each longitudinal strut rests against the lead body in a retracted position, and each anchoring unit is configured and arranged to have a deployed position in which the first and second attachment rings are positioned closer together with the longitudinal struts extending away from the lead body to contact patient tissue and anchor the lead within the patient tissue.

2. The electrical stimulation lead of claim 1, wherein the anchoring unit is disposed proximal to all of the plurality of electrodes.

3. The electrical stimulation lead of claim 1, wherein the anchoring unit is configured and arranged such that, in the deployed position, the longitudinal struts extend perpendicularly away from the lead body.

4. The electrical stimulation lead of claim 1, wherein the first attachment ring comprises an outer ring surface, an interior surface, and a side surface extending between the outer ring surface and the interior surface and the second attachment ring comprises an outer ring surface, an interior surface, and a side surface extending between the outer ring surface and the interior surface; wherein at least one of the longitudinal struts comprises a biasing portion attached to the outer ring surface of the first attachment ring and extending outwardly away from the outer ring surface of the first attachment ring, the at least one of the longitudinal struts further comprising an attachment portion attached to the side surface of the second attachment ring.

5. The electrical stimulation lead of claim 1, wherein at least one of the longitudinal struts comprises a thinner portion having a smaller lateral width than an adjacent portion of the longitudinal strut and attached to the first attachment ring, wherein, in the deployed position, the longitudinal strut preferentially bends at the thinner portion.

6. The electrical stimulation lead of claim 1, wherein each of the longitudinal struts comprises a longitudinal edge and serrations extending along the longitudinal edge.

7. The electrical stimulation lead of claim 1, wherein each of the longitudinal struts comprises two opposing longitudinal edges and serrations extending along each of the two opposing longitudinal edges.

8. The electrical stimulation lead of claim 7, wherein each longitudinal strut of the anchoring unit is configured and arranged to form, in the deployed position, a corrugated region using the serrations.

9. The electrical stimulation lead of claim 1, wherein the anchoring unit further comprises an extension portion extending from the first attachment ring to the proximal end portion of the lead body and configured and arranged for manual operation by a user when the distal end portion of the lead body is implanted.

10. The electrical stimulation lead of claim 1, wherein one of the first and second attachment rings has a flared shape and is spaced apart from the lead body at one end.

11. An electrical stimulation lead, comprising:
    a lead body having a distal end portion and a proximal end portion;
    a plurality of electrodes disposed along the distal end portion of the lead body;
    a plurality of terminals disposed along the proximal end portion of the lead body;
    a plurality of conductors disposed within the lead body, each conductor of the plurality of conductors electrically coupling each of the plurality of terminals to at least one of the plurality of electrodes; and
    an anchoring unit disposed along the distal end portion of the lead body, the anchoring unit having a first end and a second end and comprising
       a first attachment ring disposed at the first end,
       a second attachment ring disposed at the second end,
       a plurality of longitudinal struts extending linearly between, and coupled to, the first and second attachment rings, wherein at least a portion of each longitudinal strut rests against the lead body in a retracted position, and each anchoring unit is configured and arranged to have a deployed position in which the first and second attachment rings are positioned closer together with the longitudinal struts extending away from the lead body to contact patient tissue and anchor the lead within the patient tissue, and a spring coupled to at least one of the first and second attachment rings and configured and arranged to bias the anchoring unit to the deployed position.

12. The electrical stimulation lead of claim 1, wherein the anchoring unit is configured and arranged to preferentially adopt the deployed position unless constrained to adopt the retracted position.

13. The electrical stimulation lead of claim 11, wherein one of the first attachment ring or second attachment ring is fixed to the lead body and another one of the first attachment ring and the second attachment ring is slidably engaged around the lead body.

14. The electrical stimulation lead of claim 1, wherein the longitudinal struts are configured and arranged to angle toward the proximal end portion of the lead body in the deployed position.

15. An electrical stimulation system, comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed on the proximal end portion of the lead body of the electrical stimulation lead.

16. An anchoring unit having a first end and a second end, the anchoring unit comprising:

a first attachment ring disposed at the first end and configured and arranged to receive a first portion of a lead within the first attachment ring, wherein the first attachment ring comprises an outer ring surface, an interior surface, and a side surface extending between the outer ring surface and the interior surface;

a second attachment ring disposed at the second end and configured and arranged to receive a second portion of the lead within the second attachment ring, wherein the second attachment ring comprises an outer ring surface, an interior surface, and a side surface extending between the outer ring surface and the interior surface; and a plurality of longitudinal struts extending linearly between, and coupled to, the first and second attachment rings, wherein at least one of the longitudinal struts comprises a biasing portion attached to the outer ring surface of first attachment ring and extending outwardly away from the outer ring surface of the first attachment ring, the at least one of the longitudinal struts further comprising an attachment portion attached to the side surface of the second attachment ring.

17. The electrical stimulation lead of claim 11, wherein the first attachment ring comprises an outer ring surface, an interior surface, and a side surface extending between the outer ring surface and the interior surface and the second attachment ring comprises an outer ring surface, an interior surface, and a side surface extending between the outer ring surface and the interior surface; wherein at least one of the longitudinal struts comprises a biasing portion attached to the outer ring surface of the first attachment ring and extending outwardly away from the outer ring surface of the first attachment ring, the at least one of the longitudinal struts further comprising an attachment portion attached to the side surface of the second attachment ring.

18. The anchoring unit of claim 16, wherein at least one of the longitudinal struts comprises a thinner portion having a smaller lateral width than an adjacent portion of the longitudinal strut and attached to the first attachment ring, wherein the longitudinal strut is configured and arranged to preferentially bend at the thinner portion.

19. The anchoring unit of claim 16, wherein each of the longitudinal struts comprises a longitudinal edge and serrations extending along the longitudinal edge.

* * * * *